United States Patent [19]
Fujise et al.

[11] Patent Number: 5,166,200
[45] Date of Patent: Nov. 24, 1992

[54] TREATMENT OF ENDOMETRIOSIS

[75] Inventors: Nobuaki Fujise; Yasushi Yamashita; Hiroaki Takaoka; Nobuyoshi Honda; Makoto Yoshihama, all of Tochigi, Japan

[73] Assignee: Snow Brand Milk Products Company, Limited, Hokkaido, Japan

[21] Appl. No.: 683,647

[22] Filed: Apr. 11, 1991

[30] Foreign Application Priority Data

Apr. 12, 1990 [JP] Japan .................................. 2-97379

[51] Int. Cl.⁵ .............................................. A61K 31/56
[52] U.S. Cl. .................................. 514/177; 514/180; 514/178
[58] Field of Search ............... 552/582, 583, 590, 615, 552/621, 623; 514/177, 178, 182, 180

[56] References Cited

FOREIGN PATENT DOCUMENTS 0265119 4/1988 European Pat. Off. .
0300062 1/1989 European Pat. Off. .

OTHER PUBLICATIONS

Patent Abstracts of Japan, vol. 13, No. 379 (C-628)[372-7]Aug. 22, 1989.
Yamamoto et al., "Inhibitory Effect of a New Androstenedione Derivative, 14α-hydroxy-4-Androstene-3,6,17-Trione (14α-OHAT) on Aromatase Activity of Human Uterine Tumors," J. Steroid Biochem., vol. 36, No. 6, pp. 517-521 (1990).
Dictionnaire des Termes Techniques de Médecine, 20th ed., pp. 414-415 (1983).
CA: 110(21)-191258n-Yoshihama et al. (May 1989).
CA: 110(23)-2148112-Nakakoshi et al. (Dec. 1989).

Primary Examiner—Frederick E. Waddell
Assistant Examiner—T. J. Criares
Attorney, Agent, or Firm—Millen, White, Zelano & Branigan

[57] ABSTRACT

A remedy for endometriosis comprising, as an active ingredient, 14α-hydroxy-4-androstene-3,6,17-trione or an ester derivative thereof, can effectively treat endometriosis by the strong aromatase-inhibitory activity without giving serious side effects.

6 Claims, No Drawings

TREATMENT OF ENDOMETRIOSIS

BACKGROUND OF THE INVENTION (1) Field of the Invention

The present invention relates to a novel method for the treatment of endometriosis.

(2) Description of the Prior Art

Endometriosis appears as a product of atopic proliferation of endometrium. Internal endometriosis includes adenomyosis of uterus and endosalpingosis, and external endometriosis includes endometriosis of pelvic cavity and ectopic endometriosis. Endometriosis appears at a high incidence in females of 20-45 years old and its incidence has shown a steady increase in recent years, i.e., endometriosis is seen in 15-20% of females of 20-35 years old. Endometriosis is generally accompanied by dysmenorrhea and has a close relation to acyesis. Endometriosis is generally treated by pseudomenopausal treatment using danazol [Bonzal (trade name) manufactured by Tokyo Tanabe Seiyaku]. Buserelin [Suprecur (trade name) manufactured by Hoechst Japan] which is a LH-RH derivative has also been tried. However, danazol gives side effects such as dyshepatia, masculinization and the like and buserelin gives side effects such as hyposexuality, hot flushes and the like.

When medicinal treatments show no effect, a surgical treatment such as hysterectomy, lesion removal or the like is adopted but is not a desirable approach in view of the patient's response, the after effect, etc.

Therefore, development of an effective a drug is desired.

Meanwhile, the present inventors have for many years studied aromatase (a steroidogenesis enzyme) inhibitor.

It is known that 14α-hydroxy-4-androstene-3,6,17-trione and ester derivatives thereof have a strong aromatase-inhibitory activity. These compounds are disclosed in Japanese Patent Application Laid-Open Nos. 192794/1988, 131193/1989, etc. The present inventors studied the pharmacological activities of the compounds and found that the aromatase-inhibitory activity shown by the compounds is effective for treatment of endometriosis.

SUMMARY OF THE INVENTION

The object of the present invention is to provide a remedy for endometriosis showing a strong aromatase-inhibitory activity.

The above object of the present invention can be achieved by treating endometriosis with, 14α-hydroxy-4-androstene-3,6,17-trione or an ester derivative thereof.

DETAILED DESCRIPTION OF PREFERRED EMBODIMENTS

The active ingredients used in the present invention are represented by the following structural formulas

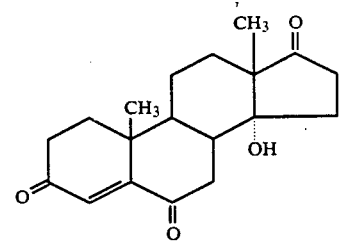

6-OA

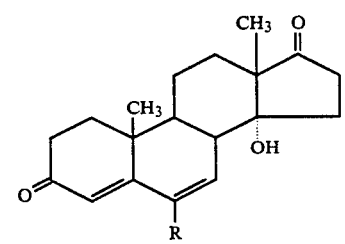

Enol Ester derivative of 6-OA wherein R represents a —OCOR$_1$ group (R$_1$ is a lower alkyl group, an aryl group or an aralkyl group).

In the present invention, the lower alkyl group refers to a straight or branched carbon chain of 1-6 carbon atoms, unless otherwise specified. Therefore, the lower alkyl group includes, for example, methyl, ethyl, propyl, butyl, pentyl, hexyl, isobutyl, tert-butyl and isopropyl. The aryl group includes, for example, phenyl and tolyl. The aralkyl group includes, for example, benzyl and phenylethyl. The ester group thereof (—OCOR$_1$) includes, for example, the followings.

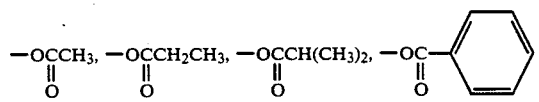

The ester derivative is preferably a propionate (6-OAp) or a benzoate (6-OAb).

The above compounds can be synthesized by the methods described in Japanese Patent Application Laid-Open Nos. 192794/1988 and 131193/1989. That is, 14α-hydroxy-4-androstene-3,6,17-trione is synthesized from 6β,14α-dihydroxy-4-androstene-3,17-dione according to an ordinary oxidation reaction (for example, Jones' oxidation reaction) and then is reacted with propionic anhydride or benzoyl chloride to obtain a propionate or a benzoate.

These compounds are made into pharmaceutical preparations and then administered in forms such as by an oral agent, suppository, injection and the like. In preparing an oral agent, there are used carriers such as mannitol, lactose, starch, magnesium stearate, cellulose, glucose, saccharose and the like; and an absorption accelerator, etc. can be added as necessary. The oral agent can be used in combination with a conventional remedy for endometriosis.

In the treatment of endometriosis, the active compound is administered daily for 1-6 months in an amount of 10 mg to 1 g per day.

The remedy for endometriosis according to the present invention specifically inhibits aromatase (a steroidogenesis enzyme) to reduce estradiol (Ez), thereby exhibiting a therapeutic effect for endometriosis This action mechanism is different from those of danazol and buserelin, and the present remedy for endometriosis provides very high utility.

6-OA has very low toxicity and animal tests indicated its $LD_{50}$ is more than 2,000 mg/kg. The ester derivatives of 6-OA have low toxicity as well. Therefore, these compounds can provide a very safe remedy.

The present invention is hereinafter described in more detail by way of Examples and Test Examples.

| Example 1 (Tablets) | |
|---|---|
| 14α-Hydroxy-4-androstene-3,6,17-trione (6-OA) | 200 mg |
| Hydroxy propyl cellulose (HPC) | 30 mg |
| Lactose | 67 mg |
| Magnesium stearate | 3 mg |
| Total | 300 mg |

The above components were mixed to prepare tablets so that each tablet contained them in the above amounts.

| Example 2 (Tablets) | |
|---|---|
| 6-OA | 200 mg |
| HPC | 30 mg |
| Hydroxy propyl methyl cellulose (TC-5) | 6 mg |
| Lactose | 61 mg |
| Magnesium stearate | 3 mg |
| Total | 300 mg |

The above components were mixed to prepare tablets so that each tablet contained them in the above amounts. In this case, an aqueous TC-5 solution was used as a binder, and granules were prepared according to a wet method and made into tablets.

| Example 3 (Tablets) | |
|---|---|
| 14α-Hydroxy-androsta-4,6-diene-3,17-dione-6-propionate (6-OAp) | 235.4 mg* |
| HPC | 30 mg |
| Lactose | 80.6 mg |
| Magnesium stearate | 4 mg |
| Total | 350 mg |

(*Equivalent to 200 mg of 6-OA.)

The above components were mixed to prepare tablets so that each tablet contained them in the above amounts.

| Example 4 (Tablets) | |
|---|---|
| 6-OAp | 235.4 mg |
| HPC | 30 mg |
| TC-5 | 6 mg |
| Lactose | 74.6 mg |
| Magnesium stearate | 4 mg |
| Total | 350 mg |

The above components were mixed to prepare tablets so that each tablet contained them in the above amounts. In this case, an aqueous TC-5 solution was used as a binder, and granules were prepared according to a wet method and made into tablets.

| Example 5 (Capsules) | |
|---|---|
| 6-OA | 200 mg |
| HPC | 30 mg |
| Lactose | 116 mg |
| Magnesium stearate | 4 mg |
| Total | 350 mg |

The above components were mixed and packed into hard capsules specified by the Japanese Pharmacopoeia, to obtain each capsule containing the above components in the above amounts.

| Example 6 (Capsules) | |
|---|---|
| 6-OA | 200 mg |
| HPC | 30 mg |
| TC-5 | 8 mg |
| Lactose | 108 mg |
| Magnesium stearate | 4 mg |
| Total | 350 mg |

The above components were mixed and packed into hard capsules specified by the Japanese Pharmacopoeia, to obtain each capsule containing the above components in the above amounts. In this case, an aqueous TC-5 solution was used as a binder, and granules were prepared according to a wet method and packed into capsules.

| Example 7 (Capsules) | |
|---|---|
| 6-OAp | 235.4 mg |
| HPC | 30 mg |
| Lactose | 130.6 mg |
| Magnesium stearate | 4 mg |
| Total | 400 mg |

The above components were mixed and packed into hard capsules specified by the Japanese Pharmacopoeia, to obtain each capsule containing the above components in the above amounts.

| Example 8 (Capsules) | |
|---|---|
| 6-OAp | 235.4 mg |
| HPC | 30 mg |
| TC-5 | 8 mg |
| Lactose | 122.6 mg |
| Magnesium stearate | 4 mg |
| Total | 400 mg |

The above components were mixed and packed into hard capsules specified by the Japanese Pharmacopoeia, to obtain each capsule containing the above components in the above amounts. In this case, an aqueous TC-5 solution was used as a binder, and granules were prepared according to a wet method and packed into capsules.

TEST EXAMPLE 1

In this Test Example, effects of administration of 6-OA and 6-enol ester compounds thereof on estradiol (Ez) reduction were examined.

Test method

Test (1) Comparison by subcutaneous administration

20 SD strain female rats of 8-week old were used as test animals. They were divided into four groups each consisting of 5 rats. To all the rats was subcutaneously injected pregnant mare serum gonatropin (PMSG) in an amount of 100 IU/body once every other day (6 times in total). In the beforenoon of the next day of the final (6th) administration of PMSG, 0.5 ml of a solvent, 50 mg/kg of 6-OA, 50 mg/kg of 6-OAp and 50 mg/kg of 6-OAb were subcutaneously administered to group I (control group), group II, group III and group IV, respectively.

After 3 hours from the administration, the rats were subjected to abdomen opening under etherization and then to exsanguination from the main vein. The blood collected from each rat was subjected to serum separation, and the Ez in the serum was determined by radioimmunoassay.

A physiological saline solution containing 0.3% of hydroxy propyl cellulose (HPC) was used as the solvent. 6-OA, 6-OAp and 6-OAb were each suspended in the solvent in such a concentration that the administration amount of the resulting suspension per rat became 0.5 ml.

Test (2) Comparison by oral administration

The type, age, number and grouping of test animals were the same as in Test (1).

All of the rats were subcutaneously injected with PMSG, in the same manner as in Test (1), in an amount of 100 IU/body once every other day (6 times in total).

Before noon of the next day of the final (6th) administration of PMSG, 0.5 ml of a solvent, 100 mg/kg of 6-OA, 100 mg/kg of 6-OAp and 100 mg/kg of 6-OAb were orally administered to group I (control group), group II, group III and group IV, respectively.

Aftr 6 hours from the administration, the rats were subjected to exsanguination. The blood collected from each rat was subjected to serum separation, and the Ez in the serum was determined by radioimmunoassay.

The solvent used was the same as in Test (1). 6-OA, 6-OAp and 6-OAb were each suspended in the solvent in such a concentration that the administration amount of the resulting suspension per rat became 0.5 ml.

Results

The Ez concentrations in serum of Test (1) and Test (2) are shown in Table 1 and Table 2.

TABLE 1

| | Test (1) Subcutaneous administration | | | |
|---|---|---|---|---|
| | I (HPC) | II (6-OA) | III (6-OAp) | IV (6-OAb) |
| Average | 0.572 | 0.262 | 0.230 | 0.390 |
| S.D. | ±0.079 | ±0.049 | ±0.035 | ±0.083 |
| | | | | (unit: ng/ml) |

TABLE 2

| | Test (2) Oral administration | | | |
|---|---|---|---|---|
| | I (HPC) | II (6-OA) | III (6-OAp) | IV (6-OAb) |
| Average | 0.522 | 0.291 | 0.226 | 0.422 |
| S.D. | ±0.072 | ±0.038 | ±0.036 | ±0.041 |
| | | | | (unit: ng/ml) |

Conclusion

The 6-OA group, the 6-OAp group and the 6-OAb group, as compared with the control group, showed a strong Ez-reducing effect in both cases of subcutaneous administration and oral administration. The 6-OAp group showed a stronger Ez-reducing effect than the 6-OA group and the 6-OAb group.

TEST EXAMPLE 2

In this Test example, effect of administration of 6-OAp on model rats of endometriosis was examined.

SD strain female rats of 7-week old weighing 170–210 g were used as test animals. In these rats, an endometrial segment (about 5 mm×5 mm) was removed from the left uterine horn and autoplanted under the left renal capsule, and formation of cysts in the transplanted endometrium was examined. Those rats which had developed cysts of 0.5–2.0 mm in height in the transplanted endometrium, were used for test.

The rats were divided into three groups. To group I (control group) was orally administered a physiological saline solution containing 0.3% of hydroxy propyl cellulose (HPC) daily in an amount of 0.5 ml/day. To group II was orally administered 6-OAp daily in an amount of 100 mg/kg/day. In this case, 6-OAp was suspended in a physiological saline solution containing 0.3% of HPC in such a concentration that the administration amount of the resulting suspension per rat became 0.5 ml. Group III (positive control) was subjected to ovary removal.

Each rat was subjected to abdomen opening after 3 weeks from the start of administration or after the ovary removal and examined for the presence of cysts.

Chi-square test was used for the statistical analysis of the test data obtained.

The results of the above test are shown in Table 3.

TABLE 3

| | 6-OAp administration | | | |
|---|---|---|---|---|
| | Cysts present | Cysts absent | Total | Disappearance |
| Control group | 20 rats | 2 rats | 22 rats | 9% |
| 6-OAp group* | 13 | 9 | 22 | 41 |
| Ovary-removed group** | 0 | 9 | 9 | 100 |

*There is a significant difference (significant level: 5% relative to control group).
**There is a significant difference (significant level: 1% relative to control group).

6-OAp was effective for experimental endometriosis of rats when orally administered daily for 3 weeks in an amount of 100 mg/kg/day.

The present invention provides a remedy for endometriosis employing 14α-hydroxy-4-androstene-3,6,17-trione or 6-enol ester derivative thereof. This remedy has an action mechanism different from those of conventional remedies for endometriosis and can treat endometriosis effectively without serious side effects.

As a result, endometriosis can be treated effectively without any surgical treatment.

What is claimed:

1. A method for treating endometriosis, which comprises administering to a woman suffering therefrom an effective amount of 14α-hydroxy-4-androstene-3,6,17-trione represented by the following general formula (I) or an enol ester derivative thereof represented by the following general formula (II)

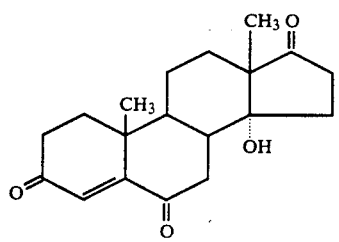 (I)

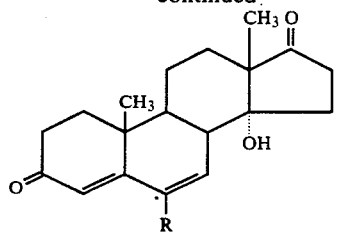 (II)

wherein R represents a —OCOR$_1$ group in which R$_1$ is lower alkyl, aryl or aralkyl.

2. The method according to claim 1, wherein the compound of Formula (I) or Formula (II) is administered orally.

3. The method according to claim 1, wherein the compound administered is 14α-hydroxy-4-androstene-3,6,17-trione.

4. The method according to claim 1, wherein the compound administered is 14α-hydroxy-androsta-4,6-diene-3,17-dione-6-propionate.

5. The method of claim 4, wherein the compound is administered orally.

6. The method of claim 5, wherein the compound administered is 14α-hydroxy-androsta-4,6-diene,3-17-dione-6-benzoate.